US011207411B2

(12) United States Patent
Lee et al.

(10) Patent No.: US 11,207,411 B2
(45) Date of Patent: Dec. 28, 2021

(54) STABILIZED PREPARATION OF INTERFERON BETA VARIANT

(71) Applicant: ABION INC., Seoul (KR)

(72) Inventors: Heejung Lee, Seoul (KR); Nam Ah Kim, Incheon (KR)

(73) Assignee: ABION INC., Seoul (KR)

( * ) Notice: Subject to any disclaimer, the term of this patent is extended or adjusted under 35 U.S.C. 154(b) by 275 days.

(21) Appl. No.: 16/340,083

(22) PCT Filed: Sep. 28, 2017

(86) PCT No.: PCT/KR2017/010826
§ 371 (c)(1),
(2) Date: Apr. 5, 2019

(87) PCT Pub. No.: WO2018/066891
PCT Pub. Date: Apr. 12, 2018

(65) Prior Publication Data

US 2019/0247506 A1 Aug. 15, 2019

(30) Foreign Application Priority Data

Oct. 6, 2016 (KR) ........................ 10-2016-0129208

(51) Int. Cl.

| | |
|---|---|
| ***A61K 47/18*** | (2017.01) |
| ***A61K 38/21*** | (2006.01) |
| ***A61K 47/12*** | (2006.01) |
| ***A61K 47/26*** | (2006.01) |
| ***A61P 31/12*** | (2006.01) |
| ***A61K 9/00*** | (2006.01) |
| ***A61K 9/08*** | (2006.01) |
| ***A61K 9/19*** | (2006.01) |
| ***A61K 47/10*** | (2017.01) |

(52) U.S. Cl.
CPC .......... *A61K 47/183* (2013.01); *A61K 9/0029* (2013.01); *A61K 9/0053* (2013.01); *A61K 9/08* (2013.01); *A61K 9/19* (2013.01); *A61K 38/21* (2013.01); *A61K 38/215* (2013.01); *A61K 47/10* (2013.01); *A61K 47/12* (2013.01); *A61K 47/18* (2013.01); *A61K 47/26* (2013.01); *A61P 31/12* (2018.01)

(58) Field of Classification Search
None
See application file for complete search history.

(56) References Cited

U.S. PATENT DOCUMENTS

| | | | | |
|---|---|---|---|---|
| 2007/0248674 A1 | 10/2007 | Del Curto | | |
| 2008/0050338 A1* | 2/2008 | DiBiase | A61P 37/00 | 424/85.4 |
| 2010/0003721 A1* | 1/2010 | Shin | A61P 31/12 | 435/69.51 |
| 2015/0368333 A1* | 12/2015 | Crotts | A61P 43/00 | 424/133.1 |

FOREIGN PATENT DOCUMENTS

| | | | |
|---|---|---|---|
| CN | 1313148 | C | 5/2007 |
| EP | 3948358 | B2 | 10/1999 |
| EP | 1809661 | B1 | 7/2007 |
| EP | 2234645 | B1 | 10/2010 |
| KR | 10-2003-0097825 | A | 12/2003 |
| KR | 10-2006-0011976 | A | 2/2006 |
| KR | 10-2006-0039132 | A | 5/2006 |
| KR | 10-2007-0030855 | A | 3/2007 |
| KR | 10-2007-0052363 | A | 5/2007 |
| KR | 10-2010-0099298 | A | 9/2010 |
| WO | 02080976 | A2 | 10/2002 |
| WO | 2015134406 | A1 | 9/2015 |

OTHER PUBLICATIONS

International Search Report (ISR) for PCT/KR2017/010826, dated Apr. 6, 2019.
First Office action for corresponding Chinese application No. 201780075339.X, dated Mar. 1, 2021, Chinese Patent Office.
European Search Report for corresponding European application No. 17858685.5, dated May 12, 2020, European Patent Office.

* cited by examiner

*Primary Examiner* — Gary B Nickol
*Assistant Examiner* — Jegatheesan Seharaseyon
(74) *Attorney, Agent, or Firm* — Lucas & Mercanti, LLP

(57) ABSTRACT

The present invention relates to a stabilized pharmaceutical preparation of R27T, the preparation comprising a human interferon beta variant (R27T), an acetate buffer, arginine, trehalose, Poloxamer 188, and methionine. The stabilized R27T pharmaceutical preparation according to the present invention is obtained by the development of a preparation having a novel composition through the substitution of mannitol with trehalose in the composition of a preparation containing mannitol, which was previously studied by the present inventors. It was confirmed that the preparation can remedy a disadvantage of the protein aggregate increase due to the mixing and addition of mannitol and arginine HCl and can improve thermodynamic/structural stability and the resulting stability during the long-term storage, and thus it is expected that the preparation can be advantageously used in the prevention, alleviation, and treatment of multiple sclerosis, cancer, autoimmune diseases, viral infectious diseases, HIV infectious diseases, hepatitis C, rheumatoid arthritis, and the like.

6 Claims, 4 Drawing Sheets

Specification includes a Sequence Listing.

FIG. 1

```
1     ATG ACC AAC AAG TGT CTC CTC CAA ATT GCT CTC CTG TTG TGC TTC TCC ACT ACA GCT CTT
       M   T   N   K   C   L   L   Q   I   A   L   L   L   C   F   S   T   T   A   L

           1
61    TCC ATG AGC TAC AAC TTG CTT GGA TTC CTA CAA AGA AGC AGC AAT TTT CAG TGT CAG AAG
       S   M   S   Y   N   L   L   G   F   L   Q   R   S   S   N   F   Q   C   Q   K

      20                              27
121   CTC CTG TGG CAA TTG AAT GGG AGG CTT GAA TAT TGC CTC AAG GAC AGG ATG AAC TTT GAC
       L   L   W   Q   L   N   G   R   L   E   Y   C   L   K   D   R   M   N   F   D
                                      ↓
      40                              T
181   ATC CCT GAG GAG ATT AAG CAG CTG CAG CAG TTC CAG AAG GAG GAC GCC GCA TTG ACC ATC
       I   P   E   E   I   K   Q   L   Q   Q   F   Q   K   E   D   A   A   L   T   I

      60
241   TAT GAG ATG CTC CAG AAC ATC TTT GCT ATT TTC AGA CAA GAT TCA TCT AGC ACT GGC TGG
       Y   E   M   L   Q   N   I   F   A   I   F   R   Q   D   S   S   S   T   G   W

      80
301   AAT GAG ACT ATT GTT GAG AAC CTC CTG GCT AAT GTC TAT CAT CAG ATA AAC CAT CTG AAG
       N   E   T   I   V   E   N   L   L   A   N   V   Y   H   Q   I   N   H   L   K

      100
361   ACA GTC CTG GAA GAA AAA CTG GAG AAA GAA GAT TTT ACC AGG GGA AAA CTC ATG AGC AGT
       T   V   L   E   E   K   L   E   K   E   D   F   T   R   G   K   L   M   S   S

      120
421   CTG CAC CTG AAA AGA TAT TAT GGG AGG ATT CTG CAT TAC CTG AAG GCC AAG GAG TAC AGT
       L   H   L   K   R   Y   Y   G   R   I   L   H   Y   L   K   A   K   E   Y   S

      140
481   CAC TGT GCC TGG ACC ATA GTC AGA GTG GAA ATC CTA AGG AAC TTT TAC TTC ATT AAC AGA
       H   C   A   W   T   I   V   R   V   E   I   L   R   N   F   Y   F   I   N   R

      160
541   CTT ACA GGT TAC CTC CGA AAC TGA AGA TCT CCT AGC CTG TCC CTC TGG GAC TGG ACA ATT
       L   T   G   Y   L   R   N  Stop
```

STABILIZED PREPARATION OF INTERFERON BETA VARIANT

TECHNICAL FIELD

The present invention relates to a stabilized pharmaceutical preparation of R27T, the preparation comprising a human interferon beta variant (R27T), an acetate buffer, arginine, trehalose, Poloxamer 188, and methionine.

BACKGROUND ART

Interferons (IFNs) exhibit anti-viral activity as a type of cytokine and have a function of suppressing cell proliferation and regulating innate immune responses. IFNs are classified into IFN-α, IFN-β and IFN-γ according to cellular origin (leukocytes, fibroblasts, T cells). Among them, interferon-beta (IFN-β) is a spherical protein having 5 alpha-helices (α-helices), which is 22 kD in size, and the size becomes 18 kD when the sugar chain is removed. Studies on the clinical application of IFN-β have been actively conducted, IFN-β has been particularly highlighted as an agent for mitigating, reducing, or treating symptoms of multiple sclerosis, and further, through various studies, study results that IFN-β is effective for treating cancer, autoimmune diseases and viral infectious diseases, diseases associated with HIV, hepatitis C, rheumatoid arthritis, and the like with various immunological activities such as anti-viral activity, cell growth suppression, lymphocyte cytotoxicity increasing activity, immunoregulatory activity, activity of inducing or suppressing differentiation of target cells, activation of macrophages, activity for increasing production of cytokines, activity for increasing effects of cytotoxic T cells, and activity for increasing natural killing cells have been reported.

Human IFN-β is also a type of glycoprotein, and since the sugar chain moiety linked to the protein plays an important role in the activity of the protein, in the case of a glycoprotein, the activity of the protein may increase when a sugar chain is added. That is, it is known that protein glycosylation may affect a lot of biochemical characteristics such as stability, solubility, intracellular trafficking activity, pharmacokinetics and antigenicity.

Thus, an example has been reported in which a sugar chain is introduced into natural human IFN-β as a glycoprotein to prepare a human IFN-β variant whose activity or function is increased or improved (Korean Patent No. 10-0781666). The human IFN-β variant R27T used in the present invention is a recombinant human IFN-β variant (hereinafter, referred to as rhINF-β) designed by substituting arginine (Arg) at position 27 with threonine (Thr) for additional glycosylation of position 25 of IFN-β 1a, and exhibits effects of increasing stability, decreasing a protein aggregation tendency, and increasing half-life when compared with the wild-type INF-β 1a (Rebif). That is, R27T is a biobetter of rhINF-β produced for additional glycosylation through site-directed mutagenesis.

Meanwhile, one of the major issues in the development of protein drugs is to produce a product having a long shelf life for 24 months or more by imparting sufficient chemical, physical and biological stability. However, due to various intrinsic susceptibilities in a protein degradation pathway, the complexity of protein structures having various levels, such as macromolecules and secondary, tertiary, and quaternary structures of proteins, it still remains a difficult problem to achieve high stability.

30 years or more have passed since the first approval and successful production of insulin as the first recombinant peptide hormone in 1982, and subsequently, numerous successful cases of recombinant protein/peptide drugs have been reported until now. However, in the process of developing biopharmaceuticals, particularly in the formulation of biopharmaceuticals, difficulties are still faced due to various factors such as protein aggregation, physicochemical instability, low half-life, low solubility, and pharmacokinetic properties.

In particular, protein aggregation is one of the major issues easily occurring in almost all biopharmaceutical processes, but the reason is that therapeutic proteins are structurally/thermodynamically unstable in solution during storage. Since therapeutic proteins are susceptible to structural changes caused by various factors during purification, processing, and storage, the aforementioned problems may be exacerbated when proteins are exposed to high temperature, maximum/minimum pH, shear strain, and surface adsorption. In addition, since protein-based biopharmaceuticals have the possibility of physical degradation such as formation of insoluble particles due to unfolding, aggregation, and non-native aggregation, optimization of a preparation system is required such as a stable pH range, an appropriate buffer system, and the development of excipients in order to avoid protein aggregation or physical degradation and maximize stability.

Therefore, the present inventors tried to develop a stabilized pharmaceutical preparation with enhanced storage and thermodynamic/structural stability of the human IFN-β variant.

DISCLOSURE

Technical Problem

In order to solve the problems in the related art, as a result of intensive studies to develop a pharmaceutical preparation capable of enhancing the stability of R27T which is a human interferon beta variant, the present inventors developed a stabilized R27T preparation having a novel composition in which storage and thermodynamic/structural stability are improved and the formation of an R27T protein aggregate is decreased as compared to existing preparations, thereby completing the present invention based on this finding.

Therefore, an object of the present invention is to provide a stabilized pharmaceutical preparation of a human interferon beta variant (R27T) having a novel composition.

However, a technical problem to be achieved by the present invention is not limited to the aforementioned problem, and other problems that are not mentioned may be clearly understood by those skilled in the art from the following description.

Technical Solution

To achieve the object of the present invention, the present invention provides a stabilized pharmaceutical preparation of a human interferon beta variant (R27T), comprising the following:

(a) a human interferon beta variant (R27T), (b) an acetate buffer at a concentration of 5 to 100 mM, (c) arginine at a concentration of 10 to 150 mM, (d) trehalose at a concentration of 50 to 300 mM, (e) Poloxamer 188 at a concentration of 0.1 to 10 mg/mL, and (f) methionine at a concentration of 0.5 to 5 mM.

As an embodiment of the present invention, the human interferon beta variant (R27T) may include an N-linked sugar chain at an asparagine residue which is amino acid 25 by substituting arginine which is amino acid 27 of the human interferon beta with threonine.

As another embodiment of the present invention, the acetate buffer may be included at a concentration of 10 to 30 mM.

As still another embodiment of the present invention, the acetate buffer may have a pH within a range of 3.6 to 4.4.

As yet another embodiment of the present invention, the arginine may be included at a concentration of 50 to 100 mM.

As yet another embodiment of the present invention, the trehalose may be included at a concentration of 150 to 250 mM.

As yet another embodiment of the present invention, the Poloxamer 188 may be included at a concentration of 0.1 to 1 mg/mL.

As yet another embodiment of the present invention, the methionine may be included at a concentration of 0.5 to 2 mM.

As yet another embodiment of the present invention, the stabilized pharmaceutical preparation may have a hydrogen ion concentration index (pH) within a range of 3.6 to 4.4.

As yet another embodiment of the present invention, the stabilized pharmaceutical preparation may be for the prevention or treatment of a disease selected from the group consisting of multiple sclerosis, cancer, autoimmune diseases, viral infectious diseases, HIV infectious diseases, hepatitis C, and rheumatoid arthritis.

As yet another embodiment of the present invention, the stabilized pharmaceutical preparation may be for oral or parenteral administration.

As yet another embodiment of the present invention, the stabilized pharmaceutical preparation may be a liquid or lyophilized formulation.

Further, the present invention provides a pharmaceutical composition for preventing or treating one or more diseases selected from the group consisting of multiple sclerosis, cancer, autoimmune diseases, viral infectious diseases, HIV infectious diseases, hepatitis C, and rheumatoid arthritis, the composition comprising a pharmaceutically effective amount of the stabilized preparation.

In addition, the present invention provides a method for preventing or treating one or more diseases selected from the group consisting of multiple sclerosis, cancer, autoimmune diseases, viral infectious diseases, HIV infectious diseases, hepatitis C, and rheumatoid arthritis, the method comprising a step of administering a pharmaceutically effective amount of the stabilized preparation to an individual.

Furthermore, the present invention provides a use of the stabilized preparation for preventing or treating one or more diseases selected from the group consisting of multiple sclerosis, cancer, autoimmune diseases, viral infectious diseases, HIV infectious diseases, hepatitis C, and rheumatoid arthritis.

Advantageous Effects

The stabilized R27T pharmaceutical preparation according to the present invention is obtained by the development of a preparation having a novel composition through the substitution of mannitol with trehalose in the composition of a preparation containing mannitol, which was previously studied by the present inventors. It was confirmed that the preparation can remedy a disadvantage of the protein aggregate increase due to the mixing and addition of mannitol and arginine HCl and can improve thermodynamic/structural stability and the resulting stability during long-term storage, and thus it is expected that the preparation can be advantageously used in the prevention, alleviation, and treatment of multiple sclerosis, cancer, autoimmune diseases, viral infectious diseases, HIV infectious diseases, hepatitis C, rheumatoid arthritis, and the like.

DESCRIPTION OF DRAWINGS

FIG. 1 illustrates genes and protein sequences of a human interferon beta variant (R27T).

MODES OF THE INVENTION

Figure 2:
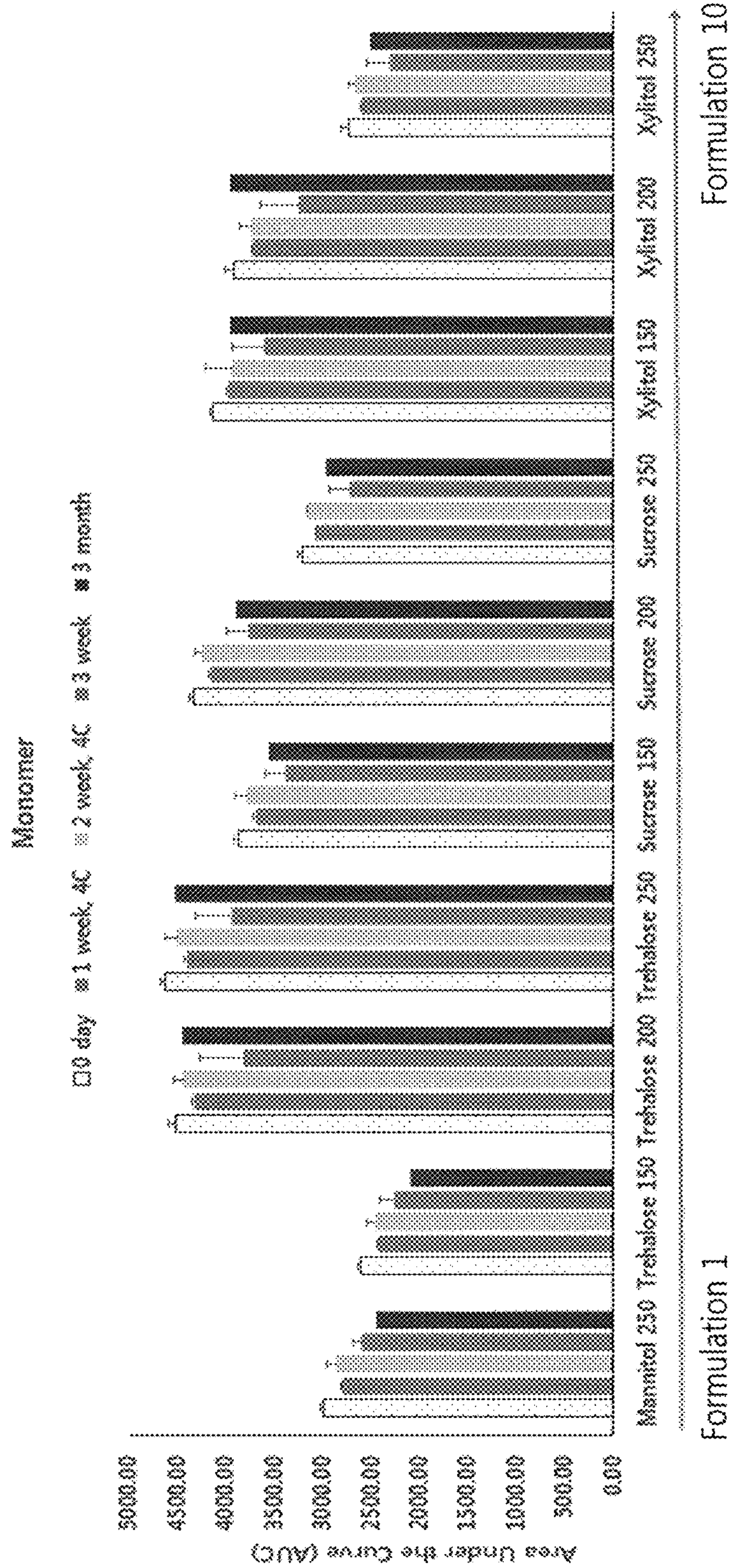
FIG. 2 is a result of evaluating the storage stability of a preparation by measuring an amount of a residual monomer through size exclusion chromatography (SEC) after a total of 10 preparations of a R27T preparation (preparation to which excipients of 250 mM mannitol, 50 mM arginine HCl, 0.5 mg/mL Poloxamer 188, and 1 mM methionine are added) prepared by adding mannitol and preparations prepared by adding trehalose, sucrose, or xylitol at a concentration of 150, 200, and 250 mM, respectively, instead of mannitol, are refrigerated at a concentration of 0.1 mg/mL and 4° C. for 0, 1 week, 2 weeks, 3 weeks, and 3 months.

The present invention relates to a stabilized pharmaceutical preparation of R27T, the preparation comprising a human interferon beta variant (R27T), an acetate buffer, arginine, trehalose, Poloxamer 188, and methionine.

Hereinafter, the present invention will be described in detail.

The present inventors selected a 20 mM acetate buffer with a pH of 3.8±0.2 using a fundamental buffer system which is optimized for R27T through prior studies to develop a stabilized pharmaceutical preparation of a human interferon beta variant R27T, and confirmed through experiments in which various excipients for enhancing the stability of R27T were added that a preparation prepared by adding mannitol, arginine HCl, Poloxamer 188, and methionine could enhance the stability of R27T as compared to existing preparations. However, the mixed composition of mannitol and arginine HCl has a disadvantage in that when the mixed composition is stored at high concentration and high temperature, stability is decreased as with existing preparations, and in order to overcome the disadvantage, the present inventors developed a stabilized pharmaceutical preparation of R27T having a new composition capable of enhancing the stability of R27T by screening an excipient capable of replacing mannitol.

Therefore, the present invention provides a stabilized pharmaceutical preparation of a human interferon beta variant (R27T), comprising a human interferon beta variant (R27T), an acetate buffer at a concentration of 5 to 100 mM, arginine at a concentration of 10 to 150 mM, trehalose at a concentration of 50 to 300 mM, Poloxamer 188 at a concentration of 0.1 to 10 mg/mL, and methionine at a concentration of 0.5 to 5 mM.

In an embodiment of the present invention, after a R27T preparation having the same composition was prepared by using trehalose, sucrose, and xylitol in order to find a mannitol substitute capable of enhancing the storage stability of R27T as compared to the aforementioned R27T preparation prepared by adding mannitol, the stability of each preparation was determined after each preparation was stored at low concentration. As a result, it was confirmed that when trehalose was used, storage stability and reversibility were significantly increased, and that even when sucrose and xylitol were used, the reversibility of the preparation was relatively increased (see Example 2).

In another embodiment of the present invention, as a result of determining the stability and anti-viral activity of the R27T preparation to which trehalose or xylitol was added as an excipient by replacing mannitol based on the result of Example 2, it was confirmed that a preparation prepared by adding trehalose during storage at high temperature had the best stability against heat and the best stability according to an increase in concentration, and exhibited thermodynamic/structural stability and anti-viral activity similar to those of a preparation using mannitol (see Example 3).

In still another embodiment of the present invention, as a result of analyzing the stability of the preparation through the change in protein aggregate in a composition in which mannitol or trehalose was mixed with arginine, it was confirmed that mannitol increased the protein aggregation when mixed with arginine as compared to the case where arginine was not present, whereas trehalose rather decreased protein aggregation in a mixed composition with arginine (see Example 4).

Through the results of the embodiments of the present invention, it was confirmed that the novel R27T stabilized pharmaceutical preparation of the present invention using trehalose as an excipient is excellent in stability as compared to existing R27T preparations using mannitol, and thus the novel R27T stabilized pharmaceutical preparation may be usefully used for the treatment of various diseases by using interferon beta.

As used herein, the term "interferon-beta (IFN-β)" refers to not only a human-originated fibroblast interferon obtained by isolation from a biological fluid or obtained from eukaryotic or prokaryotic host cells by a DNA recombinant technique, but also salts, functional derivatives, variants, analogs, and active fractions thereof. Preferably, IFN-β is intended to mean Interferon beta-1a.

As used herein, trehalose used as a substitute for mannitol refers to a non-reducing disaccharide where two molecules of D-glucose are linked via a 1→1 alpha bond, and chemically, there are three types of an α,α type, an α,β type, and a β,β type, and trehalose that may be naturally obtained is an α,α type. Trehalose was first discovered in ergot of rye, is present in large amounts in bacteria or yeast and was observed even in body fluids and eggs of insects, and is known to play an important role as an energy source or a storage carbohydrate of insects.

As used herein, the term "stabilized preparation" is a preparation such that the degree of degradation, denaturation, aggregation, and loss of biological activity of the proteins contained therein is controlled to an acceptable degree and is not increased to an unacceptable level over time. Preferably, the preparation maintains R27T activity to at least about 60%, preferably at least about 70%, and more preferably at least about 80% for up to 24 months.

As used herein, the term "buffer" refers to a solution of a compound having an effect of adjusting or maintaining the pH of a preparation such that the pH of the preparation falls within a preferred pH range. In the present invention, a buffer suitable for adjusting pH is not limited, but buffer may include phosphoric acid, acetic acid, citric acid, and histidine, is preferably an acetate buffer at a concentration of 5 to 100 mM, and more preferably, may be included at a concentration of 10 to 30 mM, even more preferably 20 mM.

In the present invention, the stabilized pharmaceutical preparation of R27T may be prepared by including: steps of dialyzing a solution including a human interferon variant R27T by using a solution including an acetate buffer at a concentration of 5 to 100 mM and an excipient; and filtering the dialysate.

In the present invention, as an excipient, arginine at a concentration of 10 to 150 mM, trehalose at a concentration of 50 to 300 mM, Poloxamer 188 at a concentration of 0.1 to 10 mg/mL, and methionine at a concentration of 0.5 to 5 mM may be added, and more preferably, arginine at a concentration of 50 to 100 mM, trehalose at a concentration of 150 to 250 mM, Poloxamer 188 at a concentration of 0.1 to 1 mg/mL, and methionine at a concentration of 0.5 to 2 mM may be added.

When the stabilized pharmaceutical preparation of R27T of the present invention is prepared as a "liquid formulation", a preferred solvent is water or sterile water for injection, and may be a monodose or multidose. It is preferred that the liquid R27T preparation for multidose of the present invention includes a bacteriostatic agent such as phenol, m-cresol, p-cresol, o-cresol, chlorocresol, benzyl alcohol, alkylparabens (methyl, ethyl, propyl, butyl, and the like), benzalkonium chloride, benzethonium chloride, sodium dehydroacetate, and thimerosal. The bacteriostatic agent is used in a content that may yield a concentration that is effective for maintaining an essentially bacteria free preparation (suitable for injection) over the multidose injection period, which is about 12 or 24 hours to about 12 days, preferably about 6 to 12 days. It is preferred that the bacteriostatic agent is present at a concentration of about 0.1% to about 2.0% (mass of the bacteriostatic agent/mass of the solvent).

The preparation of the present invention may optionally further include not only a diluent, an excipient, and a carrier, but also a physiologically/pharmaceutically acceptable additive, for example, a free-fluidizing agent, an emulsifier, a stabilizer, a preservative, a colorant, an antifoaming agent, and an anticaking agent.

The pharmaceutically acceptable carrier is not particularly limited, but may include physiological saline, polyethylene glycol, ethanol, vegetable oil, isopropyl myristate, and the like.

Further, the present invention provides a method for treating a disease such as multiple sclerosis, cancer, autoimmune diseases, viral infectious diseases, HIV infectious diseases, hepatitis C, and rheumatoid arthritis by administering a pharmaceutically effective amount of a sterilized preparation to an individual.

As used herein, the "individual" refers to a subject in need of treatment for a disease, and more specifically, refers to a mammal such as a human or a non-human primate, a mouse, a rat, a dog, a cat, a horse, and a cow.

Regarding the "pharmaceutically effective amount", it is obvious to those skilled in the art that the range thereof may be adjusted variously depending on a patient's body weight, age, gender, health status, diet, administration time, administration method, and excretion rate, severity of disease, and the like.

A preferred dosage of the preparation of the present invention varies depending on the condition and body weight of a patient, the degree of a disease, the form of drug, the administration route, and the duration, but may be appropriately selected by those skilled in the art. However, the preparation is administered preferably at 0.001 to 100 mg/kg of body weight daily, and more preferably at 0.01 to 30 mg/kg of body weight daily. The dose may be administered once a day or may be divided into several doses.

The preparation of the present invention may be administered to a mammal such as a rat, a mouse, livestock, and a human via various routes. The administration method is not limited, and the preparation of the present invention may be administered by oral, rectal, or intravenous, intramuscular, hypodermic, intrauterine, or intra-cerebroventricular injections.

Hereinafter, preferred Examples for helping the understanding of the present invention will be suggested. However, the following Examples are provided only to more easily understand the present invention, and the contents of the present invention are not limited by the following Examples.

EXAMPLES

Example 1. Experimental Method 1-1. Size Exclusion Chromatography (SEC)

An R27T sample was analyzed by using an Agilent high performance liquid chromatography system (Agilent HPLC 1260, Santa Clara, Calif., USA) equipped with a TSK-GEL G3000SWXL SEC column (TOSOH Bioscience, PA, USA) and a diode detector (DAD). In order to isolate water-soluble R27T particles, mobile-phase A (a 0.1% aqueous trifluoroacetic acid (TFA) solution, 100 mM NaCl) and mobile phase B (0.1% TFA acetonitrile, 100 mM NaCl) were flowed at a flow rate of 0.5 mL/min at a ratio of 4:6. A region analyzed as a peak of the multimer in the sample was calculated along with a region of the aqueous aggregate. The difference in total area of the R27T sample between the first measurement and the subsequent measurements (sum of the areas of all peak regions in the chromatogram result) was defined to be due to the formation of an insoluble aggregate during the measurements. The remaining proportions of the respective types (insoluble aggregates, monomers, and protein fragments) were calculated as a peak area compared to the initial time, and the storage period was graphed as the X-axis. In this case, the equation for calculating the remaining proportion is as follows.

$$\text{Remaining amount } (\%) = (a_t - A_0) \times 100$$

In the equation, $a_t$ refers to the area of the protein peak at each time, and $A_0$ refers to the initial area of each protein peak. The error bar refers to a standard deviation (SD) for three measurements.

1-2. Differential Scanning Calorimetry (DSC)

In order to perform the thermodynamic stability evaluation of the R27T sample, a VP-DSC Microcalorimeter (Microcal, Northampton, Mass., USA) was used. The experiment was performed at a heating rate of 1° C. per minute from 15° C. to 120° C. and repeated three times in total. The DSC experimental results were standardized by subtracting a baseline measured using a buffer finally measured and calculating the concentration of protein present in the sample.

The R27T measurement results set a baseline for zero adjustment of the result through a linear baseline adjustment. In this case, the procedure of setting the baseline for zero adjustment of the sample is complicated because the procedure is disturbed by the aggregation and precipitation phenomenon caused by heating, and the present invention allowed the most stable result to be obtained regardless of the type of sample or the determination of the user in the repeated experiments by selecting a prior baseline option.

The final calorimetric record was plotted with the excess specific heat (cal/° C.mol) on the Y axis and the temperature on the X axis (° C.). From these results, the protein transition temperature ($T_m$) was calculated.

1-3. Cytopathic Effect (CPE) Assay

In order to evaluate the anti-viral effect of each R27T stabilized preparation, A549 cells as a lung cancer cell line were aliquoted at $3\times10^5$ cells/mL into a 96-well plate, 100 µl of a medium including the cells was treated with 100 µl of each preparation, and the cells were cultured at 37° C. for 22 hours. After the supernatant was removed on day 2 and the cells were treated with 100 uL of encephalomyocarditis virus (EMCV) at a concentration of 1000 TCID50/mL and cultured at 37° C. for 22 hours, the titer as compared to the standard was calculated by removing the supernatant on day 3 and staining the viable cells to measure absorbance at 570 nm.

Example 2. Comparison and Analysis of Stability of R27T Preparation According to Excipients 2-1. Preparation of R27T Preparation The present inventors prepared a preparation for enhancing the stability of an interferon beta variant R27T by adding excipients of 20 mM acetate buffer with a pH of 3.8, mannitol, arginine HCl, Poloxamer 188, and methionine to the interferon variant through prior studies. Furthermore, the present invention intends to develop a preparation which is more stable than a mixed preparation to which mannitol and arginine HCl are added by discovering an excipient capable of substituting for mannitol used as an existing interferon stabilizer.

For this purpose, as shown in the following Table 1, a total of 10 types of R27T preparations were prepared by using the same composition and concentration as those of the other excipients along with the composition (1(F5)) of the preparation including mannitol prepared in prior studies, adding various concentrations (150, 200, or 250 mM) of trehalose known to be present in large amounts in bacteria or yeast and observed even in body fluids and eggs of insects as a non-reducing disaccharide where two molecules of D-glucose are linked via a 1→1 alpha bond instead of mannitol, or adding various concentrations (150, 200, or 250 mM) of sucrose or xylitol determined to substitute for mannitol in prior studies, and experiments for comparison and analysis of the stability of the preparation were performed.

TABLE 1

| Formulation | pH 3.8 Sodium acetate buffer 20 mM | | | |
|---|---|---|---|---|
| | Diluent | Aggregation suppressor | Surfactant | Anti-oxidant |
| 1(F5) | Mannitol 250 mM | Arginine HCl 50 mM | Poloxamer 188 0.5 mg/mL | Methionine 1 mM |
| 2 | Trehalose 150 mM | Arginine HCl 50 mM | Poloxamer 188 0.5 mg/mL | Methionine 1 mM |
| 3 | Trehalose 200 mM | Arginine HCl 50 mM | Poloxamer 188 0.5 mg/mL | Methionine 1 mM |
| 4 | Trehalose 250 mM | Arginine HCl 50 mM | Poloxamer 188 0.5 mg/mL | Methionine 1 mM |
| 5 | Sucrose 150 mM | Arginine HCl 50 mM | Poloxamer 188 0.5 mg/mL | Methionine 1 mM |
| 6 | Sucrose 200 mM | Arginine HCl 50 mM | Poloxamer 188 0.5 mg/mL | Methionine 1 mM |
| 7 | Sucrose 250 mM | Arginine HCl 50 mM | Poloxamer 188 0.5 mg/mL | Methionine 1 mM |
| 8 | Xylitol 150 mM | Arginine HCl 50 mM | Poloxamer 188 0.5 mg/mL | Methionine 1 mM |
| 9 | Xylitol 200 mM | Arginine HCl 50 mM | Poloxamer 188 0.5 mg/mL | Methionine 1 mM |
| 10 | Xylitol 250 mM | Arginine HCl 50 mM | Poloxamer 188 0.5 mg/mL | Methionine 1 mM |

2-2. SEC: Analysis of Amount of Monomer

In order to evaluate the storage stability of each R27T preparation prepared in Example 2-1, after the 10 preparations were refrigerated at a concentration of 0.1 mg/mL and 4° C. for 0, 1 week, 2 weeks, 3 weeks, and 3 months, respectively, the amount of a residual monomer was measured by using the size exclusion chromatography method in Example 1-1.

As a result, as illustrated in FIG. 2, it was confirmed that in spite of the same initial concentration, the content of a monomer was shown to be different according to each preparation (formulation). When trehalose was added instead of mannitol, reversibility was significantly increased, and consequently, it was confirmed that storage stability was significantly increased. Further, the higher the used concentration of trehalose was, the higher the reversibility was, and it can be seen that especially when trehalose was added at a concentration of 200 and 250 mM, the change in amount of a monomer was very small even after cold-storage for 3 months. Meanwhile, it was confirmed that even in the case of the preparation to which sucrose and xylitol were added at 150 or 200 mM, the reversibility of the preparation was relatively increased.

Example 3. Verification of Stability and Anti-Viral Activity of R27T Preparation According to Addition of Trehalose 3-1. SEC: Analysis of Amount of Monomer Based on the results in Example 2, an additional stability analysis was performed mainly on the preparation using trehalose confirmed to enhance the cold-storage stability of the R27T preparation as compared to the case where mannitol was used. More specifically, the R27T preparation was prepared by adding mannitol at a concentration of 250 mM, or adding trehalose or xylitol at a concentration of 200 or 250 mM, and the detailed compositions of the preparations are shown in the following Table 2.

TABLE 2

| No. | Formulation | pH 3.8 Sodium acetate buffer 20 mM | | |
|---|---|---|---|---|
| 1 | Mannitol 250 mM | Arginine HCl 50 mM | Poloxamer 188 0.5 mg/mL | Methionine 1 mM |

TABLE 2-continued

| No. | Formulation | pH 3.8 Sodium acetate buffer 20 mM | | |
|---|---|---|---|---|
| 2 | Trehalose 200 mM | Arginine HCl 50 mM | Poloxamer 188 0.5 mg/mL | Methionine 1 mM |
| 3 | Trehalose 250 mM | Arginine HCl 50 mM | Poloxamer 188 0.5 mg/mL | Methionine 1 mM |
| 4 | Xylitol 200 mM | Arginine HCl 50 mM | Poloxamer 188 0.5 mg/mL | Methionine 1 mM |
| 5 | Xylitol 250 mM | Arginine HCl 50 mM | Poloxamer 188 0.5 mg/mL | Methionine 1 mM |

First, in order to evaluate the storage stability of the 5 R27T preparations, after each preparation was stored at a high concentration of 0.64 mg/mL and at a high temperature of 37° C. for 0, 14, 21, and 28 days, the amount of a monomer was measured by the method in Example 1-1.

Figure 3:
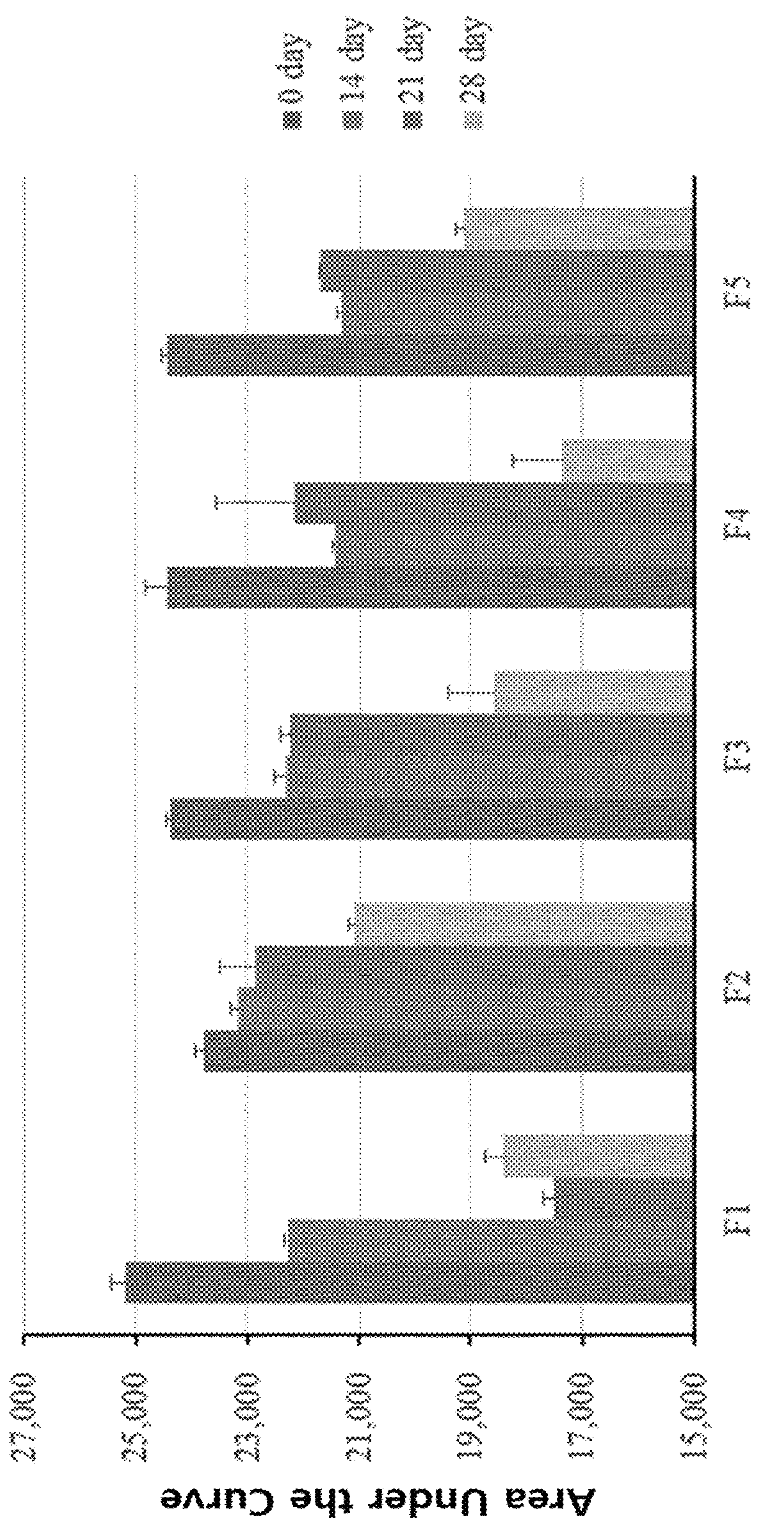
FIG. 3 is a result of evaluating the storage stability of a preparation by performing SEC to measure an amount of a residual monomer after a total of 5 preparations of the R27T preparation prepared by adding the same mannitol as in FIG. 2 and the preparations prepared by adding trehalose or xylitol at a concentration of 200 or 250 mM instead of mannitol are stored at a high temperature of 37° C. for 0, 14, 21, and 28 days.

As a result, as illustrated in FIG. 3, it was shown that as compared to the other preparations, Preparation No. 2, that is, the case where trehalose was added at 200 mM had the best stability against heat. Further, it was confirmed that the preparation also had the highest stability according to an increase in concentration, compared to the other preparations.

3-2. DSC: Analysis of Thermodynamic Stability

In addition to the analysis of the storage stability in Example 3-1, the thermodynamic/structural stability of R27T was evaluated by performing a DSC analysis on the 5 R27T preparations by the method in Example 1-2.

As a result, as illustrated in the following Table 3, it can be seen that in Preparations Nos. 1 to 3 to which mannitol or trehalose was added, $T_m$ values higher than those of Preparations Nos. 4 and 5 to which xylitol was added were exhibited, Preparations Nos. 1 to 3 exhibited similar $T_m$ values, and thus, the thermodynamic or structural stability of R27T was high in the 3 R27T preparations.

TABLE 3

| Formulation | Concentration (mg/mL) | Highest $T_m$ (° C.) |
|---|---|---|
| 1 | 0.64 | 60.60 |
| 2 | 0.64 | 60.46 |
| 3 | 0.64 | 60.28 |
| 4 | 0.64 | 50.77 |
| 5 | 0.64 | 47.77 |

3-3. CPE Assay: Analysis of Anti-Viral Activity

In addition to the analyses of the stability in Examples 3-1 and 3-2, the CPE assay was performed by the method in Example 1-3 in order to compare the anti-viral activities of the respective R27T preparations.

As a result, as illustrated in the following Table 4, it was confirmed that in the case of Preparation No. 2 to which 200 mM trehalose was added, an anti-viral activity similar to that of the preparation to which mannitol was added was exhibited.

Through the Example results, it was confirmed that when the R27T preparation prepared by adding 200 mM trehalose was compared with the preparation prepared by adding 250 mM mannitol, storage stability, structural stability, and anti-viral activity were similar or enhanced, and it can be seen that trehalose at the above concentration had an advantage sufficient for replacing mannitol.

TABLE 4

| Formulation | pH 3.8 Sodium acetate buffer 20 mM | | | | CPE Assay Result (IU/mL) |
|---|---|---|---|---|---|
| 1 | Mannitol 250 mM | Arginine HCl 50 mM | Poloxamer 188 0.5 mg/mL | Methionine 1 mM | 114,255,875 |
| 2 | Trehalose 200 mM | Arginine HCl 50 mM | Poloxamer 188 0.5 mg/mL | Methionine 1 mM | 104,797,451 |
| 3 | Trehalose 250 mM | Arginine HCl 50 mM | Poloxamer 188 0.5 mg/mL | Methionine 1 mM | 92,340,782 |
| 4 | Xylitol 200 mM | Arginine HCl 50 mM | Poloxamer 188 0.5 mg/mL | Methionine 1 mM | 88,066,849 |
| 5 | Xylitol 250 mM | Arginine HCl 50 mM | Poloxamer 188 0.5 mg/mL | Methionine 1 mM | 93,848,676 |

Example 4. Comparison and Analysis of Stability According to Presence or Absence of Arginine HCl Mixture In the R27T preparation using 200 mM trehalose finally selected as an excipient capable of substituting for mannitol through Examples 2 and 3, it was analyzed whether there is a difference in storage stability of the preparation according to the presence or absence of arginine HCl. For this purpose, as illustrated in the following Table 5, a preparation (control-1) using only an acetate buffer and an R27T preparation (control-2) to which 250 mM mannitol was added without adding arginine HCl were used as controls, and a preparation (3) to which 50 mM arginine HCl and 250 mM mannitol were added together and preparations (4 and 5) to which 200 mM trehalose was added with or without the addition of 50 mM arginine HCl were used as experimental groups. After each preparation was stored at a low concentration (0.1 mg/mL) or a high concentration (0.64 mg/mL) at a high temperature of 37° C. for 1, 7, 14, and 28 days, the degree of protein aggregation was measured through the SEC analysis of Example 1-1.

TABLE 5

| Formulation (F) | pH | 20 mM Sodium acetate buffer | | | |
|---|---|---|---|---|---|
| 1 (Control-1) | 3.8 | 20 mM Sodium acetate buffer | | | |
| 2 (Control-2) | 3.8 | | Mannitol 250 mM | Poloxamer 188 0.5 mg/mL | Methionine 1 mM |
| 3 | 3.8 | Arginine HCl 50 mM | Mannitol 250 mM | Poloxamer 188 0.5 mg/mL | Methionine 1 mM |
| 4 | 3.8 | | Trehalose 200 mM | Poloxamer 188 0.5 mg/mL | Methionine 1 mM |
| 5 | 3.8 | Arginine HCl 50 mM | Trehalose 200 mM | Poloxamer 188 0.5 mg/mL | Methionine 1 mM |

Figure 4:
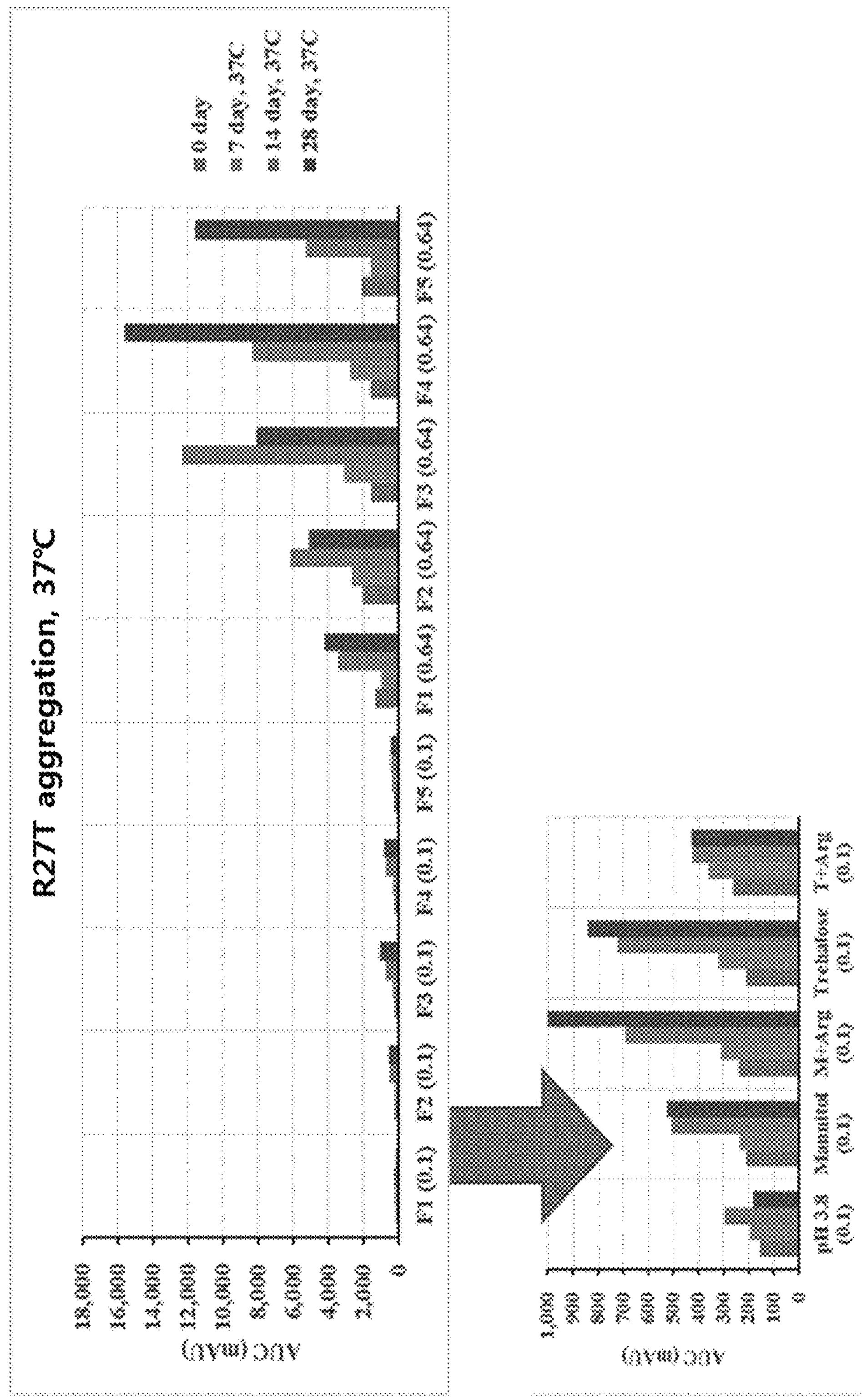
FIG. 4 is for verifying the stability of R27T according to whether arginine HCl is added to a preparation having a composition comprising mannitol or trehalose which is the same as in FIGS. 2 and 3, and is a result of measuring the protein aggregation degree through SEC analysis after each preparation is stored at a low concentration (0.1 mg/mL) or a high concentration (0.64 mg/mL) and a high temperature of 37° C. for 1, 7, 14, and 28 days.

As a result, as illustrated in FIG. 4, it was confirmed that in the case of the preparation prepared by adding mannitol, protein aggregation was increased at both the low concentration and the high concentration by the addition of arginine HCl (Comparison between F2 and F3), whereas in the case of the preparation prepared by adding trehalose, protein aggregation was decreased as compared to the case where arginine HCl was added (Comparison between F4 and F5).

Through the result, it can be seen that the preparation to which trehalose and arginine HCl was added together had better stability than the mannitol-based preparation.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

The stabilized R27T pharmaceutical preparation provided by the present invention is a preparation having a novel composition through the substitution of mannitol with trehalose in the composition of a preparation containing mannitol, which was previously studied by the present inventors. It was confirmed that the preparation can remedy a disadvantage of the protein aggregate increase due to the mixing and addition of mannitol and arginine HCl and can improve thermodynamic/structural stability and the resulting stability during long-term storage, and thus the preparation can be advantageously used in the prevention, alleviation, and treatment of multiple sclerosis, cancer, autoimmune diseases, viral infectious diseases, HIV infectious diseases, hepatitis C, rheumatoid arthritis, and the like.

Sequence Listing Free Text

```
<210> 1
<211> 600
<212> DNA
<213> Type R27T IFN-beta DNA sequence
<400> 1

atgaccaaca agtgtctcct ccaaattgct ctcctgttgt gcttctccac tacagctctt     60

tccatgagct acaacttgct tggattccta caaagaagca gcaattttca gtgtcagaag    120

ctcctgtggc aattgaatgg gacgcttgaa tattgcctca aggacaggat gaactttgac    180

atccctgagg agattaagca gctgcagcag ttccagaagg aggacgccgc attgaccatc    240

tatgagatgc tccagaacat ctttgctatt ttcagacaag attcatctag cactggctgg    300

aatgagacta ttgttgagaa cctcctggct aatgtctatc atcagataaa ccatctgaag    360

acagtcctgg aagaaaaact ggagaaagaa gattttacca ggggaaaact catgagcagt    420
```

-continued

| Sequence Listing Free Text |
|---|
| ctgcacctga aaagatatta tgggaggatt ctgcattacc tgaaggccaa ggagtacagt 480 |
| cactgtgcct ggaccatagt cagagtggaa atcctaagga acttttactt cattaacaga 540 |
| cttacaggtt acctccgaaa ctgaagatct cctagcctgt ccctctggga ctggacaatt 600 |
| 600 |
| <210> 2<br><211> 187<br><212> PRT<br><213> Type R27T IFN-beta Protein sequence<br><400> 2 |
| Met Thr Asn Lys Cys Leu Leu Gln Ile Ala Leu Leu Leu Cys Phe Ser<br>1 5 10 15 |
| Thr Thr Ala Leu Ser Met Ser Tyr Asn Leu Leu Gly Phe Leu Gln Arg<br>20 25 30 |
| Ser Ser Asn Phe Gln Cys Gln Lys Leu Leu Trp Gln Leu Asn Gly Thr<br>35 40 45 |
| Leu Glu Tyr Cys Leu Lys Asp Arg Met Asn Phe Asp Ile Pro Glu Glu<br>50 55 60 |
| Ile Lys Gln Leu Gln Gln Phe Gln Lys Glu Asp Ala Ala Leu Thr Ile<br>65 70 75 80 |
| Tyr Glu Met Leu Gln Asn Ile Phe Ala Ile Phe Arg Gln Asp Ser Ser<br>85 90 95 |
| Ser Thr Gly Trp Asn Glu Thr Ile Val Glu Asn Leu Leu Ala Asn Val<br>100 105 110 |
| Tyr His Gln Ile Asn His Leu Lys Thr Val Leu Glu Glu Lys Leu Glu<br>115 120 125 |
| Lys Glu Asp Phe Thr Arg Gly Lys Leu Met Ser Ser Leu His Leu Lys<br>130 135 140 |
| Arg Tyr Tyr Gly Arg Ile Leu His Tyr Leu Lys Ala Lys Glu Tyr Ser<br>145 150 155 160 |
| His Cys Ala Trp Thr Ile Val Arg Val Glu Ile Leu Arg Asn Phe Tyr<br>165 170 175 |
| Phe Ile Asn Arg Leu Thr Gly Tyr Leu Arg Asn<br>180 185 |

SEQUENCE LISTING

<160> NUMBER OF SEQ ID NOS: 2

<210> SEQ ID NO 1
<211> LENGTH: 600
<212> TYPE: DNA
<213> ORGANISM: Artificial Sequence
<220> FEATURE:
<223> OTHER INFORMATION: Type R27T IFN-beta DNA sequence

<400> SEQUENCE: 1
atgaccaaca agtgtctcct ccaaattgct ctcctgttgt gcttctccac tacagctctt 60
tccatgagct acaacttgct tggattccta caaagaagca gcaattttca gtgtcagaag 120
ctcctgtggc aattgaatgg gacgcttgaa tattgcctca aggacaggat gaactttgac 180
atccctgagg agattaagca gctgcagcag ttccagaagg aggacgccgc attgaccatc 240
tatgagatgc tccagaacat ctttgctatt ttcagacaag attcatctag cactggctgg 300

-continued

```
aatgagacta ttgttgagaa cctcctggct aatgtctatc atcagataaa ccatctgaag    360

acagtcctgg aagaaaaact ggagaaagaa gattttacca ggggaaaact catgagcagt    420

ctgcacctga aaagatatta tgggaggatt ctgcattacc tgaaggccaa ggagtacagt    480

cactgtgcct ggaccatagt cagagtggaa atcctaagga acttttactt cattaacaga    540

cttacaggtt acctccgaaa ctgaagatct cctagcctgt ccctctggga ctggacaatt    600


<210> SEQ ID NO 2
<211> LENGTH: 187
<212> TYPE: PRT
<213> ORGANISM: Artificial Sequence
<220> FEATURE:
<223> OTHER INFORMATION: Type R27T IFN-beta Protein sequence

<400> SEQUENCE: 2

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Thr
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185
```

The invention claimed is:

1. A stabilized pharmaceutical preparation of a human interferon beta variant, comprising:
(a) a human interferon beta variant;
(b) an acetate buffer at a concentration of 10 to 20 mM;
(c) arginine at a concentration of 50 mM;
(d) trehalose at a concentration of 200 to 250 mM;
(e) Poloxamer 188 at a concentration of 0.1 to 10 mg/mL; and
(f) methionine at a concentration of 0.5 to 5 mM,
wherein
the acetate buffer has a pH within a range of 3.6 to 4.0;
the human interferon beta variant comprises substituting arginine which is amino acid 27 of the human interferon beta with threonine.

2. The stabilized pharmaceutical preparation of claim 1, wherein the Poloxamer 188 is comprised at a concentration of 0.1 to 1 mg/mL.

3. The stabilized pharmaceutical preparation of claim 1, wherein the methionine is comprised at a concentration of 0.5 to 2 mM.

4. The stabilized pharmaceutical preparation of claim 1, wherein the stabilized pharmaceutical preparation is for the treatment of a disease selected from the group consisting of multiple sclerosis, cancer, autoimmune diseases, viral infectious diseases, HIV infectious diseases, hepatitis C, and rheumatoid arthritis.

5. The stabilized pharmaceutical preparation of claim 1, wherein the stabilized pharmaceutical preparation is for oral or parenteral administration.

6. The stabilized pharmaceutical preparation of claim 1, wherein the stabilized pharmaceutical preparation is a liquid or lyophilized formulation.

* * * * *